United States Patent [19]

Novicky

[11] 4,314,068
[45] Feb. 2, 1982

[54] OXYGEN-PERMEABLE CONTACT LENS COMPOSITIONS, METHODS, AND ARTICLES OF MANUFACTURE

[75] Inventor: Nick N. Novicky, Wheeling, Ill.

[73] Assignee: George F. Tsuetaki, Chicago, Ill.

[21] Appl. No.: 172,839

[22] Filed: Jul. 28, 1980

Related U.S. Application Data

[62] Division of Ser. No. 6,725, Jan. 26, 1979, Pat. No. 4,216,303.

[51] Int. Cl.$^3$ .............................. C07F 7/08; C07F 7/18
[52] U.S. Cl. ..................................... 556/440; 556/442; 556/451
[58] Field of Search ....................... 556/442, 440, 451

[56] References Cited

U.S. PATENT DOCUMENTS

| | | | |
|---|---|---|---|
| 2,956,044 | 10/1960 | Merker | 556/440 X |
| 3,398,210 | 8/1968 | Plueddemann et al. | 556/440 X |
| 3,440,206 | 4/1969 | Pande et al. | 556/442 X |
| 3,498,824 | 3/1970 | Chadha | 556/442 X |
| 3,808,178 | 4/1974 | Gaylord | 556/440 X |
| 3,878,263 | 4/1975 | Martin | 556/440 X |
| 4,120,570 | 10/1978 | Gaylord | 556/440 X |
| 4,153,641 | 5/1979 | Deichert et al. | 556/440 X |

OTHER PUBLICATIONS

Nou, "Chemistry and Technology of Silicones", Academic Press, N.Y. (1968), p. 204.

Primary Examiner—Paul F. Shaver
Attorney, Agent, or Firm—James T. FitzGibbon

[57] ABSTRACT

Copolymers of acrylic or methacrylic materials of known type and reacted with novel, silicone-substituted acrylic and methacrylic compounds so as to produce an oxygen-permeable plastic material which is uniquely suitable for manufacturing novel corneal contact lenses. The silicone materials include high molecular weight polysiloxanylalkylesters of acrylic and methacrylic acids, made from acrylic or methacrylic ester silanes containing one or more highly substituted siloxanyl groups.

One such siloxane substituent, pentamethyldisiloxane, is prepared by a novel method. Certain of the substituted silanes are prepared using a novel compound, tris(trimethylsiloxy) acetoxysilane. The polymers made from the combination of novel and known monomers are highly permeable to oxygen and can be used to make lenses, including bifocal lenses, which are thick enough to be rugged, hard enough to provide dimensional stability, and optimum optical correction, and sufficiently permeable to oxygen to provide extended duration wearing capabilities.

A number of novel monomers are disclosed. The polymers may be made from known monomers and individual novel monomers, or from the known monomers or mixtures thereof and mixtures of the novel monomers. The finished polymers may also include conventional additives such as wetting agents and cross-linking agents.

7 Claims, No Drawings

OXYGEN-PERMEABLE CONTACT LENS COMPOSITIONS, METHODS, AND ARTICLES OF MANUFACTURE

This is a division of application Ser. No. 6,725, filed Jan. 26, 1979, now U.S. Pat. No. 4,216,303.

BACKGROUND OF THE INVENTION

The present invention relates to novel chemical compounds, polymers made from such compounds and novel materials and products made from such compounds. In particular, one important use of the materials made from the invention is the manufacture of corneal contact lenses.

In recent years, corneal contact lenses have become more and more popular in the United States and throughout the world.

The great popularity of contact lenses is easily understood. One important reason is that such lenses provide perhaps the best possible manner of achieving optical correction for the eyes. The lenses fit directly over the eye, and when properly fitted, are easily retained in place. Problems common with spectacles, such as interference with peripheral vision, moving about on the head, discomfort, and the possibility of improper interpupilary distance, are easily overcome. Contact lenses provide cosmetic advantages and afford convenience and increased safety when used in diverse pursuits, particularly sporting events.

Contact lenses, which were originally made from glass, were gradually improved as improved materials became available. Now most commonly used contact lenses are generally subdivided into two types, rigid or so-called hard contact lenses, and soft contact lenses. Each type of lens has its own advantages, but each also includes certain disadvantages.

Referring first to the advantages of hard contact lenses, these lenses provide dimensional stability, so that the characteristics of an optical prescription will remain unchanged while the lens is in use on the eye. In some cases, the eye will actually conform to the contour of the lens over a period of time so as to improve the vision of the wearer. Moreover, hard contact lenses are relatively durable in relation to soft lenses.

Hard lenses may be made with small weights embedded in their peripheries, or may be cut to a prismatic shape for meridional orientation on the eye. Any lens which can be oriented, whether a hard or a soft lens, can be made into a multifocal lens, and can be cut or ground so as to have astigmatic correction, either in single vision or multifocal form.

While hard contact lenses have the above and other advantages, some patients find such lenses somewhat uncomfortable in use, and prefer the so-called soft contact lens. These lenses fall generally into three categories, namely lenses made from silicone rubber or like materials, lenses made from "HEMA" (hydroxyethylmethacrylate) or so-called "hydrogel" lenses, and finally, lenses of the methylmethacrylate base type, modified by the addition of polymers such as cellulose acetate butyrate ("CAB"). Soft lenses readily conform to the eye and are quite comfortable in short term use. They can be made extremely thin as well as soft and pliable.

In an attempt to create lenses which are permeable to oxygen and which are therefore comfortable in prolonged or extended use, both hard and soft lenses have been made which are extremely thin, some lenses being only 0.05 to 0.06 mm thick, for example. While lenses of this thickness may be worn for extended periods, they are so thin that they are very fragile and difficult to handle. Very thin lenses can be made in bifocal configurations by providing two or more different radii of curvature on the front surface. Thicker lenses may be truncated at the bottom and/or made prismatic so that they will orient themselves on the eye. However, while theoretically attractive, lenses of this sort have been successful in actual use only occasionally, and thus are not in widespread use.

Referring now to HEMA type lenses, while these lenses possess reasonable dimensional stability, they sometimes absorb water, and hence expand, somewhat unevenly, thus assuming a distorted shape and causing slight visual distortion for the user. Thus, while HEMA lenses are reasonably satisfactory, their dimensional stability is not as good as that of hard contact lenses.

At present, there is another "trade-off" in relation to lenses intended for prolonged or extended use. Thus, when lenses are thin enough to be sufficiently permeable for comfort, they may be too delicate to be cleaned frequently, but on the other hand, if they are not cleaned frequently, proteinaceous and other deposits from the eye may form a coating on the lens which interferes with clear vision.

In view of the foregoing advantages of contact lenses, it would be even further advantageous if there were a hard contact lens material that possessed the known advantages of machinability, dimensional stability, toughness and optical clarity, and which were also sufficiently oxygen-permeable in relatively greater thicknesses to be worn by a user for an extended period, such as for several days, weeks, or even months or more. Hard contact lenses which could be worn for an extended period would eliminate common problems both with existing hard and soft type lenses. These problems include losing or misplacing the lenses because of frequent handling, contamination, and wear and tear occasioned by such handling, and the general inconvenience of locating and inserting the lenses when they are needed but not being worn.

Referring to handling, it is not uncommon for a pair of hydrogel lenses costing perhaps hundreds of dollars, to last for only about one year or so without cracking or becoming torn as a result of frequent handling. More sturdy lenses, such as known types of hard lenses, are not susceptible to tearing or cracking, but can be scratched by frequent removal and insertion, and cleaning, particularly if they are dropped occasionally. Losing the lenses is a realistic possibility which could be minimized substantially by having lenses which are removed weekly or monthly, or at greater intervals.

An improved oxygen-permeable hard contact lens which could be made in moderate thicknesses could be reasonably rugged and could provide freedom from bacterial penetration, and realize the potential of hard lenses for shape retention and optical correction while on the eye.

Referring now to prior attempts to provide polymers with increased oxygen permeability, normally, most or all such known polymers have either been too dimensionally unstable for satisfactory use, or have had other disadvantages. For example, it is known to add significant amounts of additives normally intended to increase wettability. While such materials are helpful in proper amounts, using excess amounts thereof has often tended to cause proteinaceous matter to deposit on and impair the transparency of the inner surface of the lens. This has been a particular problem with middle aged and older persons, who often use multifocal lenses which are inherently relatively thick in relation to single vision lenses.

While numerous attempts have been made to improve the oxygen permeability of both hard and soft contact lenses, the attempts have met with only limited success, particularly in thicker lenses. Moreover, many soft lens materials provide an environment which is highly suitable for bacterial growth, and this calls for sterilization procedures which in turn require the lenses to be handled frequently.

The present invention, therefore, is intended, from the standpoint of an end use product, to provide contact lens materials which are sufficiently oxygen permeable that they may be worn by the user on a greatly extended basis in relation to prior art lenses, which do not have the disadvantages associated with known prior art lenses intended for this purpose.

Referring now to its chemical aspects, the invention relates to the manufacture of copolymers of an acrylic or methacrylic material of a known type, and novel, silicone-substituted acrylic and methacrylic compounds so as to produce an oxygen-permeable plastic material which is uniquely suitable for manufacturing novel corneal contact lenses as referred to above. The expression "copolymers" is sometimes used herein for simplicity in referring to a polymer which includes two principal comonomers, although such polymer may incidentally include one or more additional, known monomers in minor amounts, for purposes such as cross-linking, increasing the wettability of the final product, or otherwise.

The copolymer compositions, and products made therefrom, are improved over counterpart prior art compositions by reasons of increased dimensional stability and improved gas permeability. Such novel compositions also retain or provide improvements in desirable prior art characteristics such as optical clarity, the ability to be cast, molded, or machined, and compatability with chemically bonded, hydrophilic materials adapted to improve the wettability of the finished product.

Preferably, the compositions comprise high molecular weight polysiloxanylalkyl esters of acrylic and methacrylic acids and other compositions as monomers, copolymerized with methacrylates or other esters of acrylic or methacrylic acids.

According to the invention, one comonomer (the "first" comonomer) is an acrylic or methacrylic ester silane, substituted with one or more highly substituted siloxanyl groups. One such typical first comonomer is a tris-trimethylsiloxysiloxanyl methacryloxyalkylsilane, which can be copolymerized with an alkyl acrylate or alkylmethacrylate, (the "second" comonomer), with this copolymer composition in turn being cross-linked to a slight degree by cross-linking monomers, and preferably further modified by the addition of small amounts of compounds intended to increase the wetability of the finished copolymer material. This basic polymerization of the novel comonomers with known comonomers occurs through a known double-bond polymerization mechanism.

A still further facet of the invention includes synthesis of a branched comonomer which includes tris-trimethylsiloxysiloxanyl groups. One, two, or three such groups are bonded to a silicon atom of an alkyl silane ester of acrylic or methacrylic acid.

A certain proportion, such as 10% to 60% of this compound, is then polymerized with one or more or other second comonomer compounds having the same or similar acrylic or methacrylic ester portion, together with the minor amounts of cross linking and wetting agents, referred to above.

One more aspect of the present invention relates to the method of making the so-called first or novel comonomers of the invention. According to this method, methylethersilanes are reacted with acetoxy derivatives of polysiloxanyl groups, using aqueous ethanoic sulfuric acid as a catalyst. The details of this method are brought out in other portions of the specification. In still another aspect, the invention relates to alternate methods of preparing the above or similar products. One alternate method comprises reacting trichloroalkylmethacrylates with an excess of pyridine and reacting the resulting intermediates with polysilanol compounds at about $-50°$ C.

Monomer is removed from these reaction mixtures by purification following removal of the low molecular weight materials, with the reaction products being purified by washing with weak alkalies, or like materials.

A typical novel comonomer compound of the present invention can be represented by the following general formula:

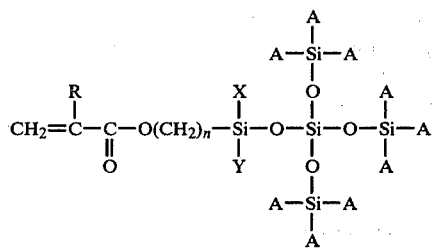

wherein R is selected from the class consisting of lower alkyl groups and hydrogen, and n is an integer from about one to three, wherein X and Y are selected from the class consisting of lower alkyl groups, cycloalkyl groups, phenyl groups (substituted or unsubstituted), polysiloxanyl groups, fluorine and Z groups; Z is a group of the structure:

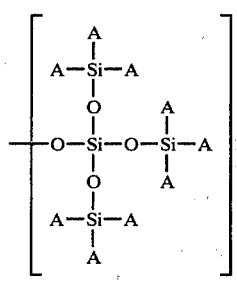

and wherein A is selected from the class consisting of lower alkyl groups and phenyl groups.

In the alkyl or phenyl ester second principal comonomer, the alkyl group contains 1 to about 20 carbon atoms, (typically one to six carbon atoms) and the phenyl ester contains a singly phenyl group.

One compound which may be used as the first principal comonomer of the present invention is a tris-trimethylsiloxysiloxanylalkyl ester comonomer such as:

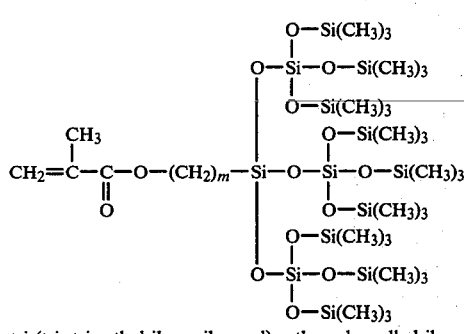

tris(tris-trimethylsiloxy-siloxanyl)methacryloxyalkylsilane n is an integer from about one to three.
Another compound is:

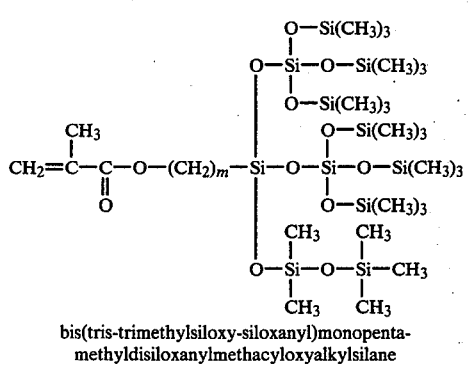

bis(tris-trimethylsiloxy-siloxanyl)monopentamethyldisiloxanylmethacyloxyalkylsilane wherein n is an integer from about one to three.
Still another compound is:

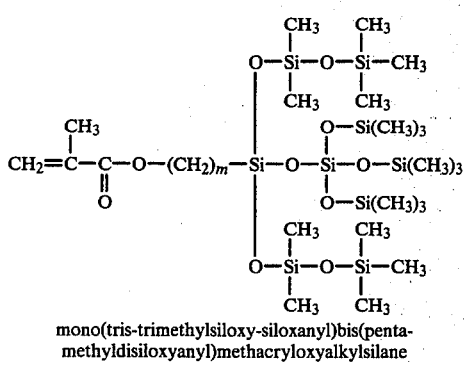

mono(tris-trimethylsiloxy-siloxanyl)bis(pentamethyldisiloxanyl)methacryloxyalkylsilane wherein n is an integer from about one to three.
Another suitable compound is:

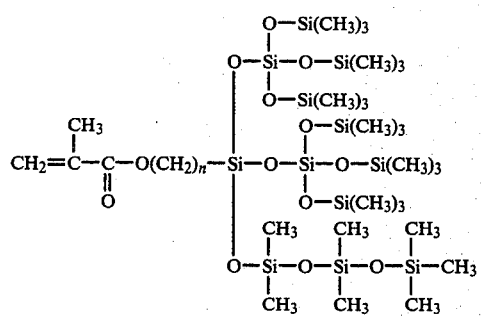

-continued
bis(tris-trimethylsiloxy-siloxanyl)mono(heptamethyltrisiloxyanyl)methacryloxyalkylsilane wherein n is an integer from about one to three.
Still another compound is:

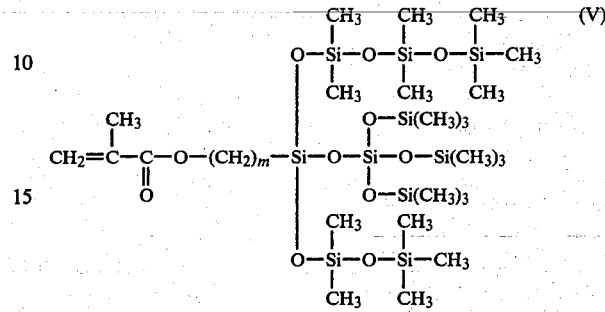

mono(tris-trimethylsiloxy-siloxanyl)mono(heptamethyltrisiloxanyl)monopentamethyldisiloxanylmethacryloxyalkylsilane wherein n is an integer from about one to three.
One more suitable compound is:

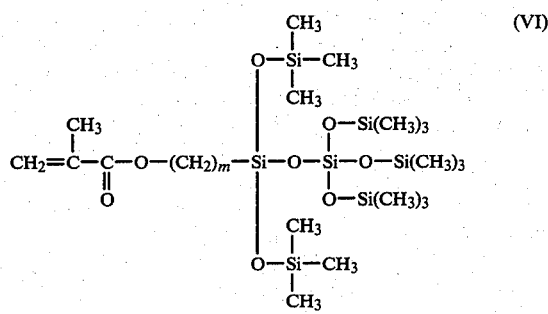

mono(tris-trimethylsiloxy-siloxanyl)bis(trimethylsiloxanyl)methacryloxyalkylsilane wherein n is an integer from about one to three.
Representative known or second comonomers which may be employed in the practice of the invention include the following:
methyl acrylate and methacrylate
ethyl acrylate and methacrylate
propyl acrylate and methacrylate
isopropyl acrylate and methacrylate
butyl acrylate and methacrylate
hexyl acrylate and methacrylate
heptyl acrylate and methacrylate
octyl acrylate and methacrylate
2-ethylhexyl acrylate and methacrylate
nonyl acrylate and methacrylate
decyl acrylate and methacrylate
undecyl acrylate and methacrylate
lauryl acrylate and methacrylate
cetyl acrylate and methacrylate
octadecyl acrylate and methacrylate
cyclohexyl acrylate and methacrylate
benzyl acrylate and methacrylate
phenyl acrylate and methacrylate
Cross-linking monomers include difunctional compounds such as:
ethyleneglycoldimethacrylate
diethyleneglycoldimethacrylate
triethyleneglycoldimethacrylate
tetraethyleneglycoldimethacrylate
polyethyleneglycoldimethacrylate and other compounds known to those skilled in the art for use in cross-linking compounds of the type referred to herein.

The wetting agents include, but are not limited to:
acrylic acid
methacrylic acid
N-vinyl 2-pyrrolidone, and
hydroxyalkyl esters of acrylic and methacrylic acids.

Referring now to the compounds referred to above, and used as intermediates to make more highly branched "tris" compounds, one such compound, for example, is tris-trimethylsiloxy-silane which is manufactured by a low temperature method. Typically, the method consists of treating one mole of trichlorosilane in a suitable anhydrous solvent with about a three molar excess of pyridine at ($-50°$ C.), and then treating the resulting intermediate product with a three equimolar amount of trimethylsilanol, which is also in a suitable anhydrous solvent, while the entire reaction mixture is maintained at about $-50°$ C. After all products are added, the mixture is brought rapidly to room temperature. From this, tris-trimethylsiloxy-silane may be removed by fractional distillation.

A still further aspect of the invention relates to the preparation of tris(trimethylsiloxy)acetoxysilane, and to a method of making such compound. The details of the manufacturing method are set out in the specification hereof; this compound is a useful intermediate in the preparation of the comonomers used as described herein.

In view of the shortcomings of prior art contact lenses and the compounds and compositions used in making them, it is an object of the present invention to provide novel monomers useful in making improved lens materials, improved polymer compositions made from such novel monomers, and improved lenses made from such polymers.

Another object of the invention is to provide novel silicone compounds used as components of polymerizable monomers.

A still further object is to provide a method of making starting or intermediate materials for making novel silicone compounds, and to provide starting and intermediate materials for other uses as well.

Yet another object is to provide highly branched or substituted silane, silanol and siloxane materials for a variety of uses, including the manufacture of copolymers, terpolymers or other polymers incorporating such materials.

Another, more specific, object is to provide a novel method of making pentamethyldisiloxane.

A still further object is to provide one or more compounds containing alkyl esters of acrylic or methacrylic acids, and incorporating one, two, or three tris(trimethylsiloxy)siloxanyl groups.

A still further object is to provide an optically useful, novel polymeric material of increased oxygen permeability with respect to prior art compounds.

Still another object is to provide a material of the foregoing type which may be formulated or synthesized so as to have a desirably high refractive index, and which can therefore be used in the manufacture of bifocal contact lenses, particularly fused bifocal contact lenses.

A still further object is to provide a composition which will make possible the manufacture of corneal contact lenses which can be worn for an extended time period while providing greatly increased comfort to the wearer.

Another object is to provide a polymeric contact lens material which is compatible with additives of known kinds used to provide other desirable end use properties.

A further object is to provide an oxygen-permeable polymer which has non-optical uses, such as forming membranes or containers for blood or other dialyzable material which can be purified by absorption of oxygen and/or transpiration or loss of other gaseous components, and for making apparatus for transferring blood or other material to and from, and through dialysis machines, for example.

A still further object is to provide a method of manufacturing copolymers incorporating the compositions made by the novel methods referred to above.

These and other objects and advantages of the invention, including those inherent therein, may be achieved in practice by carrying out the methods, and making the compounds and compositions referred to herein. The following examples, which are set forth by way of illustration and not by way of limitation, illustrate preferred methods of carrying the invention into practice.

DESCRIPTION OF THE PREFERRED EMBODIMENTS OF THE INVENTION

EXAMPLE 1

This example illustrates a new mode of synthesis of a pentamethyldisiloxane which is useful as an intermediate in preparing other compounds.

Step 1

Distilled hexamethyldisilizane (185 g.) is dissolved in 660 ml of diethylether and placed in a 3 liter, 3 necked, round bottom flask equipped with a mechanical stirrer, a thermometer and addition funnel. 132 g. of water is added to the mixture. The mixture is cooled with ice to 0° C. After flushing the system with nitrogen for 15 minutes, when the temperature reaches 0° C., 660 ml of 1.0 N hydrochloric acid is slowly added. The pH of the reaction mixture is controlled so as to remain above 5.5, after all the hydrochloric acid is added, the pH still remains above 5.5, the organic layer is separated and dried over dry magnesium sulfate for 30 minutes. Magnesium sulfate is filtered by means of a frit filter type C. Crude trimethylsilanol is analyzed by gas chromatography to determine yield of the product from the reaction.

Step 2

Dimethylchlorosilane (100 g.) is dissolved in 700 ml of dry diethylether and placed in a 2 liter, 3 necked, round bottom flask equipped with a mechanical stirrer, a thermometer and an addition funnel. The solution is cooled down to $-50°$ C. with a dry ice-isopropanol cooling bath. When the temperature has reached $-50°$ C., 95 grams (about 10% excess) of dry pyridine is added over a period of about 2½ hours, with the temperature being held at $-50°$ C. or less during pyridine addition. At the same temperature, an equimolar amount of trimethylsilanol, which can be that prepared as disclosed above, is added in a diethylether solvent, forming a white precipitate of pyridinium hydrochloride. When all the trimethylsilanol has been added, the temperature of the reaction mixture is increased rapidly to about $+30°$ C. and stirred for ½ hour. The pyridinium hydrochloride is isolated by filtration and the filter cake is washed with diethylether.

Pentamethyldisiloxane in diethylether is washed twice with water (200 ml's each). The upper (organic) layer is then separated and fractionally distilled.

The product, pentamethyldisiloxane, is distilled at about 84°–85° C. and 760 mm Hg pressure. The yield is about 70%. The pentamethyldisiloxane thus obtained is used for preparation of other intermediates by similar chemistry; as indicated below.

EXAMPLE 2

This example illustrates the synthesis of a representative important intermediate used for preparation of a polysiloxane comonomer.

Synthesis of tris-trimethylsiloxy-chlorosilane

Distilled tris-trimethylsiloxy-silane (93.7 g. (prepared by known methods) and dry pyridine (45.0 g.-slight excess) are placed in a 2 liter, 3 necked, round bottom flask and diluted to a volume of about 1200 ml. with n-Hexane. The flask is equipped with a mechanical stirrer and thermometer, and is cooled to less than 8° C. by an ice bath.

Chlorine gas is then introduced through the gas inlet tube. A white precipitate of pyridinium hydrochloride is formed. The temperature is maintained in the range of 5°–8° C., while chlorine is bubbled through the reaction mixture. Cessation of the exotherm indicates that the reaction is complete. Pyridinium hydrochloride is isolated by filtration and then discarded.

The product, tris-trimethylsiloxy-chlorosilane is recovered by fractional distillation. (B.P.=79°–80° C./11 mm Hg, $d^{20}=0.921$ g/ml $n_D^{25}=1.3923\pm0.0010$) A yield equal to about 85% of theoretical was obtained.

EXAMPLE 3

This example illustrates a synthesis of a new compound, tris-trimethylsiloxyacetoxysilane, which is useful as an intermediate in preparing other compounds referred to herein.

To a 1 liter, 3 necked, round bottom flask equipped with mechanical stirrer, a thermometer and water cooled reflux condenser whose product outlet is connected to a 500 ml's collecting flask, is added 114.9 grams of tris-trimethylsiloxy-chlorosilane, 60 g. of acetic anhydride (excess) and 4 g. of triisopropanolamine (catalyst). The mixture is refluxed for 10 hours. The resulting acetyl chloride is distilled at about 51° C. at 760 mm Hg pressure, and all low boiling materials, including an excess of acetic anhydride, are distilled off until the temperature reaches 150° C. The distillation apparatus is then connected to a vacuum line and the fraction which distills at 94°–96° C. under 5–6 mm Hg pressure is collected. A 66% yield of tris-trimethylsiloxyacetoxysilane is obtained. (B.P. 94°–96° C./5 mm Hg pressure $d_{22}=0.908$ g/ml $n_D^{25}=1.3910\pm0.001$.)

EXAMPLE 4A

This example illustrates the synthesis of a representative polysiloxanyl alkylsilane ester comonomer, mono(-tris-trimethylsiloxy-siloxanyl) bis(pentamethyldisiloxany)methacryloxypropylsilane (III).

One mole of trimethoxymethacryloxypropylsilane (248.0 g.), one mole of tris-trimethylsiloxy-acetoxysilane (346.0 g.), and two moles of acetoxypentamethyldisiloxane (412.0 g.) are mixed together in a 2 liter, 3 necked, round bottom flask equipped with a mechanical stirrer, a thermometer, and an addition funnel. The mixture is cooled to less than 10° C. by an ice cooling bath.

62.0 g. of aqueous ethanoic sulfuric acid are added to the reaction mixture over a period of 75 minutes. Then, the temperature is slowly increased to room temperature, and the reaction mixture is stirred for 15 hours. The aqueous layer which separates is removed and discarded. The organic layer is washed twice with 300 ml. of distilled water, and thereafter twice with a dilute sodium bicarbonate solution, again with distilled water once, and then dried over magnesium sulfate (anhydrous) for 2 hours. The dried monomer is purified by distilling off all low boiling materials at 80° C. and 0.1 mm Hg pressure. The purified monomer is refrigerated until used. Density of the monomer (III) is 0.983 g/ml. at 20° C.

EXAMPLE 4B

Preparation of bis(tris-trimethylsiloxy-siloxanyl)pentamethyldisiloxanylmethacryloxy-propylsilane (II)

One mole of trimethoxymethacryloxypropylsilane (248.0 g.), one mole of acetoxypentamethyldisiloxane (206.0 g.), and two moles of tris-trimethylsiloxyacetoxysilane (692.0 g.) are mixed together in a 2 liter, 3 necked, round bottom flask equipped with mechanical stirrer, thermometer and an addition funnel. Reaction is carried out in the same manner as described in Example 4A. Density of the resulting monomer is 0.981 g/ml. at 20° C. The product is refrigerated until used.

The product made from Example 4B (II) should be relatively free from unpolymerizable components for best optical clarity, as is brought out elsewhere herein.

EXAMPLE 5A

This example illustrates the preparation of a representative oxygen-permeable copolymer.

A mixture of 35 parts of the comonomer (III) of Example 4A, 65 parts of cyclohexyl methacrylate, and 0.24% by weight of the entire mixture of tert-butyl peroxydecanoate is placed in a glass dish or tube and then placed in a vacuum oven which has been purged with nitrogen. The oven is closed and the temperature is maintained at 45° C. for 24 hours. The monomers react to create a copolymer plastic which is hard, colorless, transparent and rigid. The oxygen permeability is 1430 cc.-mil/100 in.$^2$/24 hr./atm. The oxygen permeability of a disc of polymethylmethacrylate, measured in the same way is 34 cc.-mil/100 in.$^2$/24 hr./atm., while that of a disc of hydrated polyhydroxyethylmethacrylate is 250 cc.-mil/100 in.$^2$/24 hr./atm. These units and the method of taking these measurements, are known to those skilled in the art—U.S. Pat. No. 3,808,178.

EXAMPLE 5B

A mixture of 35 parts of novel comonomer of Example 4A, 60 parts of methyl methacrylate, 2 parts of N-vinyl pyrrolidone, and 3 parts of triethyleneglycoldimethacrylate and 0.24% by weight of the entire composition of t-butyl peroxydecanoate is polymerized in a polypropylene dish or tube at 48° C. for 24 hours. The resulting copolymer plastic material is machined, cut, polished, and finished into a concavoconvex lens of 0.15 mm thickness. The oxygen permeability of this lens, measured by another method or technique, is $12.4\times10^{-11}$ ml oxygen/cm$^2$/sec/155 mm Hg pressure. (155 mm Hg is the normal partial pressure of oxygen in a 760 mm Hg atmosphere.) This particular measurement was made by a "Schema-Versatae" Model 920 gas flux meter which is known and widely used in the contact lens industry.

The following Examples 6–14 illustrate the conditions of preparation and properties of copolymers which contain varying proportions of the novel comonomers of Example 4B when such comonomers are reacted with one or more of the following compounds:

methyl methacrylate (MMA)
hydroxyethylmethacrylate (HEMA)
methacrylic acid (MAA)
N-vinyl pyrrolidone (NVP)
triethyleneglycoldimethacrylate (TEGDMA)

The siloxane comonomer used in these examples is that used in Example 4B, namely, bis(tris-trimethylsiloxysiloxanyl)pentamethyldisiloxanylmethacryloxypropylsilane (II), and which is abbreviated in the table below as Compound II or Cmpd. II. The polymerization is conducted in polypropylene caps for 24 hours at the temperatures shown in the table. The table also shows the composition of each form of polymer, and the temperature at which polymerization took place. The properties of the polymer are abbreviated in the right hand corner, with the meanings of the abbreviations appearing below.

In the examples, the principal polymers are Compound II and MMA, with the compositions including one or more other compounds as indicated. HEMA provides wettability, CHMA supplements the MMA, MAA and NVP provide increased wettability, except that, where more than 4 or 5% NVP is present, a portion thereof serves as a third monomer. The TEGDMA is a crosslinking agent.

propylsilane monomer (II) of Example 4B, 50 parts of methyl methacrylate, and 5 parts of N-vinyl pyrrolidone, using tert-butylperoxypivalate as a catalyst. The polymerization is carried out at 48° C. for 24 hours. The resulting disc is colorless, transparent, hard and rigid. The oxygen permeability of the terpolymer is 1610 cc.-mil/100 in.$^2$/24 hr./atm. In this example, no difunctional cross-linking agent was used.

EXAMPLE 16

This example illustrates the preparation of a copolymer of methyl methacrylate and the novel compound (II) referred to in Example 4B.

A cylindrical plug of the copolymer is prepared by polymerizing a mixture of 40 parts of such novel comonomer (II) and 60 parts of methyl methacrylate in the presence of ter-butylperoxydecanoate at 45° C. Lenses prepared from the plug are hard, rigid, transparent, and highly oxygen permeable in relation to prior art lenses.

EXAMPLE 17

This example illustrates the preparation of a copolymer used for the production of oxygen permeable bifocal contact lenses.

A mixture of 60 parts of cyclohexylmethacrylate and 40 parts of the novel monomer (III) of Example 4A is polymerized under the conditions described in Example 16, except that the temperature is 50° C. The resulting copolymer plastic is machined to produce the bifocal or near vision segment portion of a corneal contact lens. The plastic has a high refractive index: $n_D^{25} = 1.530$. Then, a lens blank is produced in a known manner with a bifocal insert therein. The bifocal blank has portions with high and low index portions. This particular lens

| | | | COMPOSITION, WT. PERCENT | | | | | TEMP. | |
|---|---|---|---|---|---|---|---|---|---|
| Example | Cmpd. II | MMA | HEMA | CHMA | MAA | NVP | TEGDMA | °C. | PROPERTIES |
| 6 | 35 | 60 | 2 | | | | 3 | 48 | T,H,R, |
| 7 | 35 | 30 | | 30 | 4 | | 1 | 50 | T,H,R, |
| 8 | 45 | 20 | 5 | 25 | 1 | | 4 | 45 | T,H,R, |
| 9 | 38 | 29 | | 21.5 | | 8.0 | 3.5 | 46 | T,H,R, |
| 10 | 50 | 20 | | 30 | | | | 50 | T,H,SR, |
| 11 | 20 | 40 | | 40 | | | | 45 | T,H,R, |
| 12 | 40 | 40 | | 12 | 5 | 5 | 3 | 40 | T,H,R, |
| 13 | 35 | 40 | 20 | | | | 3 | 60 | ST,H,R, |
| 14 | 35 | 47.5 | | 10 | | | 3.5 | 48 | T,H,R, |

T = Transparent
H = Hard
R = Rigid
ST = Not Clear, semi-transparent
SR = Semirigid Products of the invention herein described as "hard" have a hardness, measured on the Shore D scale of about 82–90, (ASTM 2240) while polymethylmethacrylate, tested the same way, has a hardness of 90–93.

The copolymer plastic bottoms made from the materials are machined and finished in the usual manner to make contact lenses having a concave surface on one side and a convex surface on the opposite side. Then lenses are easily wetted by water and an aqueous saline solution; and all are highly oxygen permeable in relation to prior art lenses of acceptable optical quality.

EXAMPLE 15

This example illustrates the preparation and properties of a wettable, oxygen-permeable terpolymer. A disc is prepared in the manner described in Example 5 from a mixture of 45 parts of the bis(tris-trimethylsiloxysiloxanyl)pentamethyldisiloxanylmethacryloxywas then cut and finished to provide a dioptric power of +2.00 in the distant vision segment and −2.00 in the near vision segment. Such a lens is highly satisfactory from the standpoint of overall oxygen permeability, and provides excellent comfort for the wearer.

EXAMPLE 18

A bifocal contact lens was made as follows:

| Composition | Weight Percent |
|---|---|
| High Index Polymer for fused bifocal segment: | |
| $n_D^{25}$ - 1.531 | 40 parts silicone comonomer of Example 4A (III) (Compound III) |
| | 20 parts cyclohexylmethacrylate |
| | 20 parts benzylmethacrylate |
| | 15 parts N-vinyl pyrrolidone |

| Composition | Weight Percent |
|---|---|
| | 5 parts triethyleneglycoldimethacrylate |
| Low Index Polymer for remainder of lens: | |
| $n_D^{25}$ - 1.480 | 40 parts silicone comonomer of Example 4A(III) |
| | 53 parts methyl methacrylate |
| | 3 parts triethyleneglycoldimethacrylate |
| | 4 parts methacrylic acid |

EXAMPLE 19

Another bifocal lens was made as follows:

| Composition | Weight Percent |
|---|---|
| High Inedx Polymer for fused bifocal segment: | |
| $n_D^{25}$ - 1.535 | 38 parts silicone comonomer of Example 4B (II) |
| | 30 parts cyclohexyl methacrylate |
| | 30 parts benzyl methacrylate |
| | 2 parts ethyleneglycoldimethacrylate |
| Low Index Polymer for remainder of lens: | |
| $n_D^{25}$ - 1.480 | 40 parts silicone comonomer of Example 4A (III) |
| | 53 parts methyl methacrylate |
| | 3 parts triethyleneglycoldimethacrylate |
| | 4 parts methacrylic acid |

EXAMPLE 20

Another bifocal lens was made as follows:

| Composition | Weight Percent |
|---|---|
| High Index Polymer for fused bifocal segment: | |
| $n_D^{25}$ - 1.540 | 37 parts silicone comonomer of Example 4B (II) |
| | 60 parts phenyl methacrylate |
| | 3 parts triethyleneglycoldimethacrylate |
| Low Index Polymer for remainder of lens: | |
| $n_D^{25}$ - 1.480 | 40 parts silicone comonomer of Example 4A (III) |
| | 53 parts methacrylate |
| | 3 parts triethyleneglycoldimethacrylate |
| | 4 parts methacrylic acid |

EXAMPLE 21

Another bifocal lens was made as follows:

| Composition | Weight Percent |
|---|---|
| High Index Polymer for fused bifocal segment: | |
| $n_D^{25}$ - 1.540 | 38 parts silicone comonomer of Example 4A (III) |
| | 30 parts benzyl methacrylate |
| | 29 parts phenyl methacrylate |
| | 3 parts triethyleneglycoldimethacrylate |
| Low Index Polymer for remainder of lens: | |
| $n_D^{25}$ - 1.475 | 40 parts silicone monomer of Example 4A (III) |
| | 60 parts methyl methacrylate |

The foregoing examples directed to bifocal lenses illustrate that the various novel polymers of the invention can be used to make both elements of a bifocal contact lens and that the finished lens has greatly improved oxygen permeability with respect to prior art lenses. Because of this increased permeability, even relatively thick bifocal lenses, including those wherein the bifocal segment is totally surrounded by low index material, can be comfortably and safely worn for extended periods in relation to prior art lenses. The presence of even substantial percentages of the silicone comonomers which provide the increased oxygen permeability of the lenses does not in any way adversely effect the optical clarity, machinability, dimensional stability, or index of refraction of the finished product. Moreover, the finished polymer is relatively tough and scratch resistant.

Referring now to another chemical aspect of the invention, from the above examples, it can be seen that the invention, considered from the standpoint of a new contact lens material, provides a copolymer comprised of one or more comonomers which are novel in and of themselves. These include the highly substituted novel monomers referred to in the introductory portion of the specification and given Compounds Nos. I–VI, inclusive. Any one or more of these compounds or comonomers are then reacted with a class of known comonomers which have a polymerizable acrylic moiety or portion to produce the oxygen-permeable plastic. Consequently, broadly speaking, the copolymerization of these classes of comonomers, provides the basic, novel plastic material of the invention. However, as is well known to those skilled in the art, the actual plastic used in commercial practice may also further include mixtures of these known comonomers instead of the single comonomers only. Naturally, where one or more monomers are novel, the reaction product of these monomers with known comonomers will also be novel. Still further, some of the acylic monomers, while known in themselves, have not been commonly used in making lens materials.

This category includes, for example, cyclohexyl methacrylate and similar compounds which undergo the same reactions or those referred to in the above specific examples and which reactions are therefore not repeated in detail herein.

In addition to the two or more principal classes of comonomers used to make the novel plastic composition of the invention, it is well known to those skilled in the contact lens art to be desirable, but not necessary, to provide, additionally, minor amounts of other monomer materials used to cross-link the composition or increase the wettability of the finished product. However, where the novel material is not going to be used in making contact lenses, these ingredients may be left out, and other and different materials may be used as desired.

The manufacture of certain of the ingredients of the polymer, namely the various illustrated comonomers, comprises still another aspect of the invention.

More specifically, compound (I), which includes three units of the tris-trimethylsiloxy-siloxanyl group or substituent, is made as outlined in Example 4A by using the substituted acrylic propylsilane, trimethoxymethacryloxypropylsilane and reacting it with three moles of tris-methylsiloxyacetoxysilane, in the presence of ethanoic sulfuric acid, followed by the separation, rinsing and distilling steps referred to in Example 4A. The substituted acrylic or methacrylic propyl silane may be thought of or considered as a "backbone" or basic starting material onto which the siloxy functional groups are added to produce the novel monomers. Consequently, the same "backbone" is used in the case of making each different monomer, the reaction mechanism is the same, the conditions are the same, and in some cases, such as the substitution of the pentamethyldisiloxyanyl groups, portions of the starting materials are the same.

Compound (IV) is thus made by the same method, using the "backbone" acrylic starting material, trimethoxymethacryloxypropylsilane, and reacting it with two moles of the tris-trimethylsiloxyacetoxy-silane and one mole of acetoxyheptamethyltrisiloxane, a compound which is a higher homologue of the acetoxypentamethyldisiloxane referred to in Example 4.

Compound (V) is made by reacting the "backbone" compound with one mole each of acetoxyheptamethyltrisiloxane, tris(trimethylsiloxy)acetoxysilane, and acetoxypentamethyldisiloxane. Compound (V) thus has three different principal substituent groups, one containing two silicone atoms, one containing three atoms, and one containing four atoms. Conditions and other reagents are the same as those set out in Examples 4A and 4B.

Compound (VI) is created by reacting the "backbone" compound with one mole of tris-trimethylsiloxyacetoxysilane and two moles of acetoxytrimethylsilane. Conditions and other reagents are the same as those referred to in Examples 4A and 4B.

The examples referred to just above illustrate the basic nature of the reaction, namely, the provisions of a backbone or starting compound which is a substituted silane such as trimethoxymethacryloxypropylsilane. The trimethoxy group of this silane is removed by and reacts with the acetoxy portion of the substituent group to produce a by-product such as methyl acetate, with the silicone atom of the silane in the "backbone" then having the substituted siloxy group bonded thereto.

Compounds I-VI illustrate that trimethylsiloxy groups in various combinations, as well as more highly substituted groups such as the tris-trimethylsiloxy-pentamethyldisiloxyheptamethyltrisiloxy and similar groups, can be added to the backbone in various combinations.

As pointed out, and as is well known to those skilled in the art, the use of pentamethyldisiloxane as a substituent is known. The novel polymers of the present invention include comonomers which in turn include the pentamethyldisiloxane substituents, as well as the more highly branched and/or highly substituted compounds. Therefore, since some pentamethyldisiloxane is going to be used in the practice of the invention, it is also desirable to provide an improved method of making such pentamethyldisiloxane. Finally, because the reaction mechanism of making the novel monomers uses acetoxy derivations of the substitutents, a still further aspect to the invention relates to acetoxysilane compounds and their production. The acetoxy compounds undergo the class or type of reaction referred to above, namely, the elimination of an acetoxy group, and coupling a siloxy or siloxanyl group to the silicon atom bonded to the alkyl portion of the substituted acrylic or methacrylic monomer. While the basic method of manufacturing other acetoxy compounds may be suggested by certain features of the prior art, it is believed that the acetoxy compound itself is new. It is highly useful as an intermediate in preparing the novel monomers referred to herein.

Referring again to the manufacture of pentamethyldisiloxane one of the advantages of the method illustrated in Example 1 is that the yield of pentamethyldisiloxane is substantially increased over that able to be obtained from prior art methods. One reason for this is that the known and previously preferred method involves the cohydrolysis of mixed silanes, namely, the cohydrolysis of dimethylchlorosilane and trimethylchlorosilane. The process is carried out by hydrolyzing the chlorine-silicone bond and forming hydrochloric acid and the pentamethyldisiloxane. However, as with other cohydrolysis reactions using two or more different starting reagents, the reaction product comprises a mixture of the tetramethyl-, pentamethyl- and hexamethyl-disiloxanes. Since such compounds differ only slightly from each other in structure and molecular weight, subsequent separation of the desirable pentamethyldisiloxane from the other compounds is difficult, expensive, and time-consuming. According to the present invention, no such related compounds are produced. Pyridine, vinylpyridine, or similar compounds may be used to insure that the hydrochloric acid created by the reaction does not react with or otherwise interfere with the starting materials or the reaction product. It is thought that the pyridine or equivalent prevents such reaction, and when the temperature of the reaction mixture (Step 2, Example 1) is raised, the reaction begins and continues until an appropriate yield is reached.

Referring now to the polymer, plastic materials made from a monomer having one or more heptamethyltrisiloxanyl groups are suitable for use in the invention, differing only from their less substituted counterparts in molecular weights and slight physical property differences. In general, the substitution of the heptamethyltrisiloxy or other, more highly substituted groups, results in a product which is somewhat more gas permeable than a counterpart compound having a lower silicon content.

Referring again to the manufacture of the specific compounds identified as compounds Nos. I-VI, it will be understood that, as in the manufacture of other similar monomers, there are certain by-products which are made as a result of commercial or even laboratory scale manufacture of these products. For example, in an attempt to prepare the compound identified as compound II, which contains two of the tris-trimethyl- groups and one pentamethyl- group, it will be understood that a certain percentage of the yield will be a monomer having two or three pentamethyl- groups, and a certain part of the yield will be a monomer having one tris-trimethyl- group. Accordingly, the claims are not intended to exclude the presence of such compounds which exist as by-products of manufacturing the intermediates. One feature of the invention is that such by-products compounds may be satisfactorily incorporated into the plastic materials from which the lenses are to be made, even though they are not intentionally included. In addition, the by-products may include other compounds wherein there is a hydroxyl substitution on one or more silicon atoms relative to which there is or is intended to be, a siloxane group. Whereas, if sufficient effort is made, the presence of these hydroxyl-substituted compounds can be minimized or even eliminated, one feature of the invention is that although a plastic copolymer product may be made which, although incorporating varying amounts of such by-products, is still satisfactory for use as a lens material. While this aspect has not been investigated in detail, it is believed possible that such by-products might, in certain cases, aggregate as much as 10 to 15%, or perhaps more, of the intended product.

Referring now again to the preparation of pentamethyldisiloxane, the applicant has set forth the preferred method of manufacturing the same, with such method including the addition of pyridine or vinyl pyridine, for example, to the cold dimethylchlorosilane prior to the addition of the trimethylsilanol. The invention is not limited to any particular theory or mechanism of operation, it is believed possible that the pyridine, vinyl pyridine, or like compound prevents the hydrochloric acid created in the reaction from aiding or catalyzing the self-coupling of the trimethylsilanol into hexamethyl-disiloxane. Assuming that pyridine itself is used for this purpose, the resulting pyridine compound is pyridinium hydrochloride. Those skilled in the art may use other compounds serving the same purpose as pyridine or vinyl pyridine; the reaction product will then be a counterpart hydrochloride or equivalent.

It is believed that the names used herein adequately identify the compounds used in the practice of the invention. Certain compounds, in addition to being identified by name, were also identified by structure. In addition to the compounds identified by structure above, there are other compounds which, while fully identified by name, are sometimes given other or additional names, and for simplicity and accuracy, the structural formulas of these compounds are set forth below.

PVP or polyvinyl pyrrolidone is a polymer of 1-vinyl-2-pyrrolidinone:

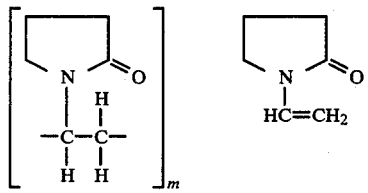

polyvinyl pyrrolidone 1-vinyl-2-pyrrolidinone (also known as N-vinyl-2-pyrrolidone)

Tris(trimethylsiloxy)acetoxysilane:

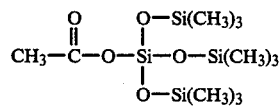

It will thus be seen that the present invention provides novel chemical compounds, compositions, methods, and articles made therefrom, such compounds, compositions, articles and methods having the novel advantages and characteristics referred to herein and others which are inherent therein. Various illustrations of the preferred practice of the invention having been set forth by way of example, it is presumed that variations and changes in the disclosed methods and compositions will occur to those skilled in the art, and that such compounds, compositions, and articles may be made, and methods practiced, without departing from the spirit of the invention or the scope of the appended claims.

I claim:

1. A new composition especially adapted for making oxygen-permeable polymers used in the production of contact lenses, said composition having the structure:

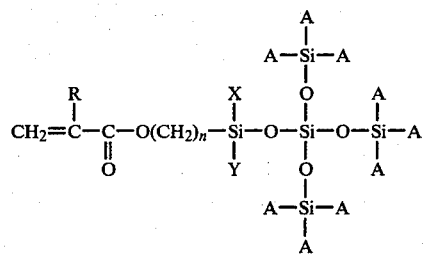

wherein R is selected from the class consisting of lower alkyl groups and hydrogen, and n is an integer from one to three, wherein X and Y are selected from the class consisting of lower alkyl groups, cycloalkyl groups, phenyl groups (substituted and unsubstituted), polysiloxanyl groups, flourine and Z groups; Z is a group of the structure:

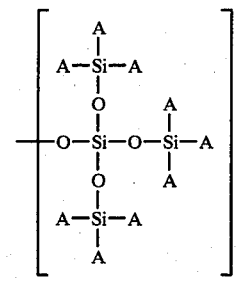

and wherein A is selected from the class consisting of lower alkyl groups and phenyl groups.

2. A new composition especially adapted for making oxygen-permeable polymers used in the production of contact lenses, said composition consisting of tris(tris-trimethylsiloxysiloxanyl)methacryloxy(lower alkyl)silane, wherein said lower alkyl group has one to three carbon atoms.

3. A new composition especially adapted for making oxygen-permeable polymers used in the production of contact lenses, said composition consisting of bis(tris-trimethylsiloxysiloxanyl)monopentamethyldisiloxanyl-methacryloxy(lower alkyl) silane, wherein said lower alkyl group has one to three carbon atoms.

4. A new composition especially adapted for making oxygen-permeable polymers used in the production of contact lenses, said composition consisting of mono(-tris-trimethylsiloxysiloxanyl)bis(pentamethyldisilox-anyl)methacryloxy(lower alkyl) silane, wherein said lower alkyl group has one to three carbon atoms.

5. A new composition especially adapted for making oxygen-permeable polymers used in the production of contact lenses, said composition consisting of bis(tris-trimethylsiloxysiloxanyl)mono(heptamethyltrisilox-anyl)methacryloxy(lower alkyl) silane, wherein said lower alkyl group has one to three carbon atoms.

6. A new composition especially adapted for making oxygen-permeable polymers used in the production of contact lenses, said composition consisting of mono(-tris-trimethylsiloxysiloxanyl)mono(heptamethyltrisilox-anyl)monopentamethyldisiloxanylmethacryloxy(lower alkyl)silane, wherein said lower alkyl group has one to three carbon atoms.

7. A new composition especially adapted for making oxygen-permeable polymers used in the production of contact lenses, said composition consisting of mono(-tris-trimethylsiloxysiloxanyl)bis(trimethylsiloxanyl)me-thacryloxy(lower alkyl) silane, wherein said lower alkyl group has one to three carbon atoms.

* * * * *

UNITED STATES PATENT AND TRADEMARK OFFICE
CERTIFICATE OF CORRECTION

PATENT NO. : 4,314,068
DATED : February 2, 1982
INVENTOR(S) : Nick N. Novicky

It is certified that error appears in the above—identified patent and that said Letters Patent is hereby corrected as shown below:

Column 9, line 62, please delete the word "any" and
    in place thereof, insert -- anyl --.

Signed and Sealed this

Twenty-second Day of June 1982

[SEAL]

*Attest:*

*Attesting Officer*

GERALD J. MOSSINGHOFF
*Commissioner of Patents and Trademarks*